(12) United States Patent
Irvin et al.

(10) Patent No.: US 8,485,454 B1
(45) Date of Patent: Jul. 16, 2013

(54) ROTATABLE AND ADJUSTABLE AIR FRESHENER

(75) Inventors: Aaron Irvin, Salt Lake City, UT (US); Nathaniel Finlay, Lehi, UT (US)

(73) Assignee: American Covers, Inc., Bluffdale, UT (US)

( * ) Notice: Subject to any disclaimer, the term of this patent is extended or adjusted under 35 U.S.C. 154(b) by 259 days.

(21) Appl. No.: 12/979,763

(22) Filed: Dec. 28, 2010

Related U.S. Application Data (60) Provisional application No. 61/291,240, filed on Dec. 30, 2009.

(51) Int. Cl.
*A61L 9/04* (2006.01)

(52) U.S. Cl.
USPC ............................................. 239/58; 239/34

(58) Field of Classification Search
USPC ................... 239/49, 51.5, 58, 71, 73, 74, 35, 239/57
See application file for complete search history.

(56) References Cited

U.S. PATENT DOCUMENTS

| | | |
|---|---|---|
| 369,878 A | 9/1887 | Palmer |
| 1,171,737 A * | 2/1916 | Madigan ........................ 239/49 |
| 1,683,545 A | 9/1928 | Harris |
| D140,109 S | 1/1945 | Pierce |
| 2,642,248 A | 6/1953 | Semon |
| D176,671 S | 1/1956 | Katz |
| 2,733,333 A | 1/1956 | Peters |
| D177,826 S | 5/1956 | Katz |
| D178,237 S | 7/1956 | Katz |
| 3,239,145 A | 3/1966 | Aurelio |
| 3,456,106 A | 7/1969 | Gluschkin |
| 3,552,632 A | 1/1971 | Wilson |
| 3,655,129 A | 4/1972 | Seiner |
| 3,847,305 A | 11/1974 | Tobin |
| 3,948,445 A | 4/1976 | Andeweg |
| 3,971,858 A | 7/1976 | Collier et al. |

(Continued)

FOREIGN PATENT DOCUMENTS

| | | |
|---|---|---|
| CA | 2077251 | 5/1993 |
| EP | 0 348 970 | 1/1990 |

(Continued)

OTHER PUBLICATIONS

About.Com Housekeeping, http://housekeeping.about.com/od/pr... affresh, Febrezee Noticeables, accessed Oct. 2, 2008, 2 pages.

(Continued)

*Primary Examiner* — Len Tran
*Assistant Examiner* — Viet Le
(74) *Attorney, Agent, or Firm* — Thorpe North & Western LLP (57) ABSTRACT

An air freshener device has a chamber containing a fragrant material pivotal with respect to a back opening in the a plate. A perimeter notch is formed in an intermediate brace and a front dial plate so that a scale on the back plate is visible. A single cartridge has a pair of scent chambers coupled together and disposed adjacent one another in a side-by-side relationship, and formed as a pair of separate and discrete vessels in a plastic sheet separated by a divider and covered by a permeable membrane. Each of the pair of vessels contains a fragrant material with a fragrance that can permeate through the permeable membrane over time.

19 Claims, 3 Drawing Sheets

U.S. PATENT DOCUMENTS

| | | |
|---|---|---|
| D246,986 S | 1/1978 | Costello |
| 4,084,079 A | 4/1978 | Costello |
| D250,041 S | 10/1978 | Schimanski |
| 4,149,675 A | 4/1979 | Van Breen et al. |
| 4,184,099 A | 1/1980 | Lindauer et al. |
| 4,226,944 A | 10/1980 | Stone et al. |
| D258,511 S | 3/1981 | Ashton |
| 4,280,649 A | 7/1981 | Montealegre |
| 4,301,949 A | 11/1981 | Palson et al. |
| 4,382,548 A | 5/1983 | van de Heijden |
| 4,391,781 A | 7/1983 | van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,874,129 A | 10/1989 | DiSapio et al. |
| 4,880,690 A | 11/1989 | Szycher et al. |
| 4,950,542 A | 8/1990 | Barker |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| 5,050,798 A | 9/1991 | Sullivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Ferguson |
| D334,975 S | 4/1993 | Bunce |
| 5,220,636 A | 6/1993 | Chang |
| D338,519 S | 8/1993 | Peterson |
| 5,234,162 A | 8/1993 | Sullivan |
| D349,157 S | 7/1994 | Rymer |
| D350,192 S | 8/1994 | Patel et al. |
| 5,368,822 A | 11/1994 | McNeil |
| 5,407,642 A | 4/1995 | Lord |
| 5,422,078 A | 6/1995 | Colon |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| 5,725,152 A | 3/1998 | Akyu |
| 5,762,549 A | 6/1998 | Scheuer et al. |
| 5,780,527 A | 7/1998 | O'Leary |
| 5,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| 5,899,382 A | 5/1999 | Hayes et al. |
| D410,540 S | 6/1999 | Pinchuk |
| D415,267 S | 10/1999 | Kauzlarich et al. |
| 5,988,520 A | 11/1999 | Bitner |
| 6,044,202 A | 3/2000 | Junkel |
| D424,677 S | 5/2000 | Chen |
| D425,190 S | 5/2000 | Morikawa |
| 6,111,055 A | 8/2000 | Berger et al. |
| 6,123,906 A | 9/2000 | Rymer |
| D432,222 S | 10/2000 | Rymer et al. |
| D437,041 S | 1/2001 | Eisenbraun |
| 6,190,607 B1 | 2/2001 | Farmer |
| 6,191,197 B1 | 2/2001 | Wang et al. |
| 6,197,263 B1 | 3/2001 | Blount |
| 6,202,938 B1 | 3/2001 | Collier |
| D440,294 S | 4/2001 | Bilek |
| D441,441 S | 5/2001 | Upson |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| 6,357,260 B1 | 3/2002 | Lutz |
| 6,374,044 B1 | 4/2002 | Freide |
| 6,375,966 B1 | 4/2002 | Maleeny et al. |
| 6,379,689 B1 | 4/2002 | Aguadisch |
| 6,391,398 B1 | 5/2002 | Pesu et al. |
| 6,416,043 B1 | 7/2002 | Eisenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,830,733 B2 | 12/2004 | Stanley, III |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,137,570 B2 | 11/2006 | Wheatley et al. |
| D535,379 S | 1/2007 | Hundertmark |
| 7,159,792 B2 | 1/2007 | Wheatley et al. |
| D544,080 S | 6/2007 | Carlson |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |
| D550,345 S | 9/2007 | Weggelaar |
| D551,333 S | 9/2007 | Wu |
| 7,285,248 B2 | 10/2007 | Yamamoto et al. |
| D554,746 S | 11/2007 | Davis et al. |
| 7,293,719 B2 | 11/2007 | Wheatley |
| D565,162 S | 3/2008 | Carlson |
| 7,344,123 B2 | 3/2008 | Pankhurst et al. |
| D565,715 S | 4/2008 | Wu |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |
| D591,415 S | 4/2009 | Wu |
| D593,670 S | 6/2009 | Valentiono et al. |
| D594,954 S | 6/2009 | Wheatley |
| 7,544,332 B2 | 6/2009 | De Silva et al. |
| D598,531 S | 8/2009 | Irvin |
| D604,825 S | 11/2009 | Brandenburg |
| D607,983 S | 1/2010 | Irvin |
| 7,651,666 B2 | 1/2010 | Adair et al. |
| 7,670,566 B2 | 3/2010 | Adair et al. |
| 7,687,037 B2 | 3/2010 | Wheatley |
| 7,687,038 B2 | 3/2010 | Wheatley |
| 7,780,094 B2 | 8/2010 | Caserta et al. |
| D629,881 S | 12/2010 | Valentino et al. |
| D631,954 S | 2/2011 | Bertassi et al. |
| D633,610 S | 3/2011 | Wu |
| D640,781 S | 6/2011 | Brandenburg |

| | | | |
|---|---|---|---|
| D642,668 S | 8/2011 | Lablaine | |
| D647,186 S | 10/2011 | Chan et al. | |
| D649,237 S | 11/2011 | Bilko et al. | |
| D667,100 S | 9/2012 | Hakim | |
| 2001/0051234 A1 | 12/2001 | Ryan et al. | |
| 2003/0097936 A1 | 5/2003 | Maleeny et al. | |
| 2003/0199421 A1 | 10/2003 | Copfer | |
| 2004/0197221 A1 | 10/2004 | Stanley, III | |
| 2004/0265164 A1 | 12/2004 | Woo et al. | |
| 2005/0084413 A1 | 4/2005 | Stanley, III | |
| 2005/0127538 A1 | 6/2005 | Fabrega et al. | |
| 2005/0169793 A1 | 8/2005 | Wheatley et al. | |
| 2006/0043216 A1 | 3/2006 | Robinson | |
| 2006/0078477 A1 | 4/2006 | Althouse et al. | |
| 2006/0279008 A1 | 12/2006 | Jursich | |
| 2007/0057084 A1 | 3/2007 | Vieira | |
| 2007/0160492 A1 | 7/2007 | Spector | |
| 2007/0231508 A1 | 10/2007 | Fand et al. | |
| 2007/0290064 A1 | 12/2007 | Majerowski et al. | |
| 2008/0099576 A1 | 5/2008 | Hart | |
| 2008/0128925 A1 | 6/2008 | Pankhurst et al. | |
| 2008/0311315 A1 | 12/2008 | Marlow | |
| 2008/0311316 A1 | 12/2008 | Marlow | |
| 2009/0008411 A1 | 1/2009 | Schumacher et al. | |
| 2009/0010813 A1 | 1/2009 | Wang et al. | |
| 2009/0173799 A1 | 7/2009 | Litten-Brown et al. | |
| 2010/0010409 A1 | 1/2010 | Bejarano | |
| 2010/0019059 A1 | 1/2010 | Bulsink et al. | |
| 2010/0065654 A1 | 3/2010 | Wheatley et al. | |
| 2010/0187327 A1 | 7/2010 | Irvin | |
| 2011/0108632 A1 | 5/2011 | Brandenburg et al. | |

FOREIGN PATENT DOCUMENTS

| | | |
|---|---|---|
| EP | 1 346 734 | 9/2003 |
| WO | WO 98/46284 | 10/1998 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |
| WO | WO 2006/010282 | 2/2006 |
| WO | WO 2006/084160 | 8/2006 |
| ZA | 20004637 | 9/2000 |

OTHER PUBLICATIONS

Aromate E-News, Innovation in Novelty Fragrance, Http://209.85.173.104/seasrch?qcach . . . , accessed Oct. 8, 2008, 2 pages.

ecrater, www.ecrater.com/product.hp? . . . , Yankee Candle Selects Two Scents Electric Fragrance Unit Macintosh/Home Sweet Home, accessed Oct. 2, 2008, 1 page.

http://decomodo.com/articles/categor/lighting/, Bamboo Pillar Candle, Jan. 8, 2008, 1 page.

http://shop.advanceautoparts.com/webapp/wcs/stores/servlet/product_6170795-P_N3004...Advance Auto Part; Arometrics Dual-Scent Vent—Juicy Strawberry and Vanilla; 1 Page; accessed Dec. 10, 2010.

http://www.bestliquidations.com/Medo_Vent Frehser.htm; BestLiquidations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark , CA 2003 copyright date on package.

Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.

U.S. Appl. No. 12/378,121, filed Oct. 29, 2010; Aaron Irvin.
U.S. Appl. No. 12/915,924, filed Oct. 29, 2010; Nathaniel Finlay.
U.S. Appl. No. 12/915,983, filed Oct. 29, 2010; Alan J. Wheatley.
U.S. Appl. No. 12/916,038, filed Oct. 29, 2010; Aaron Irvin.
U.S. Appl. No. 12/979,795, filed Dec. 28, 2010; Aaron Irvin.
U.S. Appl. No. 12/979,813, filed Dec. 28, 2010; Aaron Irvin.
U.S. Appl. No. 13/009,574, filed Jan. 19, 2011; Alan J. Wheatley.
U.S. Appl. No. 29/378,112, filed Oct. 29, 2010; Nathaniel Finlay.
U.S. Appl. No. 29/378,116, filed Oct. 29, 2010; Aaron Irvin.
www.4imprint.com/EXEC/DETAIL/FROMPRODUCTGROUP/~SKU100300/~CA100300.htm, Hot Rod Vent Stick Air Freshener (it . . . , accessed Aug. 12, 2008, 2 pages.
www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.
www.chicscents.com/Products.aspx Island Adventure Sandals; 2 pages; accessed Feb. 1, 2011.
www.chicscents.com/Products.aspx; Inspiration 3-D by Chic; 2 pages; accessed Feb. 1, 2011.
U.S. Appl. No. 12/623,007, filed Nov. 20, 2009; Alan J. Wheatley; Notice of Allowance issued Feb. 28, 2012.
U.S. Appl. No. 13/282,035, filed Oct. 26, 2011; Nathaniel Finlay.
U.S. Appl. No. 13/281,890, filed Oct. 26, 2011; Aaron Irving.
U.S. Appl. No. 13/359,726, filed Jan. 27, 2012; Aaron Irvin.
U.S. Appl. No. 29/378,112, filed Oct. 29, 2010; Nathaniel Finlay; Notice of Allowance issued Mar. 29, 2012.
U.S. Appl. No. 12/916,038, filed Oct. 29, 2010; Aaron Irvin; Notice of Allowance issued Apr. 27, 2012.
U.S. Appl. No. 29/415,358, filed Mar. 9, 2012; Aaron Irvin; Notice of Allowance issued May 29, 2012.
U.S. Appl. No. 12/693,543, filed Jan. 26, 2010; Aaron Irvin; office action dated Aug. 7, 2012.
U.S. Appl. No. 12/623,007, filed Nov. 20, 2009; Alan J. Wheatley; office action issued Jul. 29, 2011.
U.S. Appl. No. 29/394,683, filed Jun. 20, 2011; Alan J. Wheatley; notice of allowance issued Aug. 22, 2011.
U.S. Appl. No. 13/191,966, filed Jul. 27, 2011; Aaron Irvin.
U.S. Appl. No. 12/693,543, filed Jan. 26, 2010; Aaron Irvin; office action dated Dec. 18, 2012.
U.S. Appl. No. 12/979,795, filed Dec. 28, 2010; Aaron Irvin; office action dated Jan. 28, 2013.
U.S. Appl. No. 13/009,574, filed Jan. 19, 2011; Alan J. Wheatley; office action dated Jan. 11, 2013.
U.S. Appl. No. 12/979,813, filed Dec. 28, 2010; Aaron Irvin; office action dated Jan. 31, 2013.
U.S. Appl. No. 12/915,983, filed Oct. 29, 2010; Alan J. Wheatley; notice of allowance dated Feb. 20, 2013.
U.S. Appl. No. 12/979,813, filed Dec. 28, 2010; Aaron Irvin; office action dated Sep. 14, 2012.
U.S. Appl. No. 12/979,795, filed Dec. 28, 2010; Aaron Irvin; office action dated Sep. 13, 2012.
U.S. Appl. No. 29/435,389, filed Oct. 23, 2012; Aaron Irvin; notice of allowance dated Mar. 1, 2013.
U.S. Appl. No. 12/979,690, filed Dec. 28, 2010; Alan J. Wheatley, office action dated Mar. 1, 2013.
U.S. Appl. No. 12/987,662, filed Jan. 10, 2011; Alan J. Wheatley, office action dated Mar. 21, 2013.
U.S. Appl. No. 12/979,601, filed Dec. 28, 2010; Alan J. Wheatley, office action dated Mar. 1, 2013.
U.S. Appl. No. 13/009,574, filed Jan. 19, 2011; Alan J. Wheatley notice of allowance dated Apr. 3, 2013.
U.S. Appl. No. 13/359,726, filed Jan. 27, 2012; Aaron Irvin; office action dated Apr. 5, 2013.
U.S. Appl. No. 29/435,389; filed Oct. 23, 2012; Aaron Irvin; notice of allowance dated Mar. 1, 2013.
US Appl. No. 12/979,690; filed Dec. 28, 2010; Alan J. Wheatley; office action dated Mar. 1, 2013.
U.S. Appl. No. 12/987,662; filed Jan. 10, 2011; Alan J. Wheatley, office action dated Mar. 21, 2013.
U.S. Appl. No. 12/979,601; filed Dec. 28, 2010; Alan J. Wheatley, office action dated Mar. 1, 2013.
U.S. Appl. No. 13/009,574; filed Jan. 19, 2011; Alan J. Wheatley notice of allowance dated Apr. 3, 2013.
U.S. Appl. No. 13/359,726; filed Jan. 27, 2012; Aaron Irvin; office action dated Apr. 5, 2013.

* cited by examiner

ROTATABLE AND ADJUSTABLE AIR FRESHENER

PRIORITY CLAIM

Priority is claimed to copending U.S. Provisional Patent Application Ser. No. 61/291,240, filed Dec. 30, 2009, which is hereby incorporated herein by reference in its entirety.

BACKGROUND

1. Field of the Invention

The present invention relates generally to air fresheners.

2. Related Art

Various types of air fresheners have been developed. Typical air fresheners provide a single fragrance. Some air fresheners provide a single scented liquid in a container with a permeable membrane. For example, see Medo® Auto Expressions™ Vent Fresh™ scented oil air freshener. Other air fresheners provide two different scented blocks. For example, see Arometrics® Car Air Freshener dual scent vent.

SUMMARY OF THE INVENTION

It has been recognized that it would be advantageous to develop an air freshener with at least two different fragrances and the ability to select one or both of the fragrances. In addition, it has been recognized that it would be advantageous to develop an air freshener with an adjustable scent release.

The invention provides an air freshener with a back plate having a back opening therethrough. An intermediate brace is pivotally coupled to the back plate and has an intermediate opening therethrough. A front dial plate is coupled to the brace and is pivotal with the brace with respect to the back plate. A cavity is formed between the brace and the front dial plate. The cavity is exposed from behind by the back opening and the intermediate opening. At least one chamber is disposed in the cavity and contains a fragrant material, and has a permeable membrane through which a fragrance of the fragrant material can permeate over time. The at least one chamber, the intermediate brace and the front dial plate are pivotal together with respect to the back plate to selectively align the at least one chamber, the intermediate opening of the intermediate brace, or both, with the back opening in the back plate. A perimeter notch is formed in the intermediate brace and the front dial plate which is rotatable therewith respect to the back plate. A scale on the back plate is visible through the perimeter notch to indicate a relative rotational position of the at least one chamber, the intermediate opening of the intermediate brace, or both, with the back opening in the back plate.

In accordance with a more detailed aspect of the present invention, the air freshener can be configured for a single scent. The at least one chamber can be a single chamber. The intermediate opening in the intermediate brace and the back opening in the back plate can be sized less than half of the intermediate brace and back plate, respectively. The dial plate and the intermediate brace can pivot to selectively align the intermediate opening with respect to the back opening.

In accordance with a more detailed aspect of the present invention, the air freshener can be configured for dual scents. The at least one chamber can include a pair of scent chambers coupled together and disposed adjacent one another in a side-by-side relationship, and formed as a pair of separate and discrete vessels in a plastic sheet separated by a divider and covered by the permeable membrane. The pair of scent chambers can be pivotal with respect to the back plate to selectively position the pair of scent chambers with respect to the back opening between a plurality of positions, including: 1) only one of the pair of chambers aligned with the back opening, 2) only the other of the pair of chambers aligned with the back opening, and 3) a portion of both of the pair of chambers aligned with the back opening.

The present invention provides a dual scent air freshener. A single cartridge with a pair of scent chambers is coupled together and disposed adjacent one another in a side-by-side relationship, and formed as a pair of separate and discrete vessels in a plastic sheet separated by a divider and covered by a permeable membrane. Each of the pair of vessels contains a fragrant material with a fragrance that can permeate through the permeable membrane over time. A back plate is pivotally coupled with respect to the pair of chambers, and has a back opening therethrough with the permeable membrane facing the back opening. The cartridge is pivotal with respect to the back plate to selectively position the pair of scent chambers with respect to the back opening between a plurality of positions, including: 1) only one of the pair of chambers aligned with the back opening, 2) only the other of the pair of chambers aligned with the back opening, and 3) a portion of both of the pair of chambers aligned with the back opening.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIGS. 3a and b are schematic views of the dual air freshener of FIG. 1 with the top figure showing the position of the air freshener and the lower figure showing the relative position of the pair of chambers with respect to the back opening, and with the cross-hatching showing the overlap between the back opening and the chambers, or the exposure of the chambers to the back opening; with FIG. 3a showing the pair of chambers equally exposed to the back opening; and with FIG. 3b showing the pair of chambers rotated so that the second chamber is mostly aligned with respect to the back opening, and the first chamber is mostly mis-aligned with respect to the back opening; (it will be appreciated that the pair of chambers can be rotated the opposite direction to mostly align the first chamber with respect to the back opening)

FIGS. 6a and b are schematic views of the air freshener of FIG. 4 with the top figure showing the position of the air freshener and the lower figure showing the relative position of the intermediate opening and blocking plate with respect to the back opening, and with the cross-hatching showing the overlap between the intermediate and back openings, or the exposure of the chamber to the back opening; with FIG. 6a showing the intermediate opening partially exposed to the back opening (and the blocking plate partially blocking the back opening); and with FIG. 6b showing the intermediate brace rotated so that the intermediate opening is mostly aligned with respect to or exposed to the back opening; (it will be appreciated that the intermediate brace can be rotated the opposite direction to mostly align the blocking plate with respect to the back opening).

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The terms "scent" and "fragrance" are used interchangeably herein and include particular scents or even neutralizing agents.

Description

Referring to FIGS. 1-3b, a dual scent air freshener device, indicated generally at 10, in an example implementation in accordance with the invention is shown. The air freshener can be used in various different environments, such as bathrooms, wash closets, vehicles, offices, bedrooms, etc. In one aspect, the air freshener can be used in combination with a vent of an air duct through which air is forced or displaced. For example, the air freshener can be coupled to or suspended from a vehicle vent, and used in combination with forced air through the vent to disperse a scent or fragrance.

The air freshener can provide two or more different scents, either alone or in combination. The desired scents can include, for example, floral, fruit, vanilla, berry, pine, etc. The two scents can be selected to be complimentary or to have a synergistic effect. The scents can be provided by fragrant material, such as scented or fragrant oil. Thus, the air freshener can have two different fragrant materials 12a and 12b, to two fragrant materials with different scents. The scent or fragrance can disperse or leach from the fragrant material or oil over time; and the fragrant material or oil can reduce in mass or volume over time. The fragrant materials can be visible in or through the air freshener to determine the remaining amount of mass or volume. In addition, the fragrant materials can be colored, and can have different colors, to assist in selecting fragrance or fragrance combinations, as described in greater detail below.

The scent material 12a and 12b can be provided in a single cartridge 14 or scent cartridge. The cartridge can have, and the scent material can be contained in, a dual chamber vessel 16 with each different fragrant material disposed in a different one of a pair of chambers 18a and 18b coupled together and disposed adjacent one another is a side-by-side relationship. The cartridge 14, the dual chamber vessel 16, and/or the pair of chambers 18a and 18b can include a pair of separate and discrete vessels or chambers formed in a plastic sheet as cavities or bowls formed therein and separated by a divider 20. A permeable membrane 22 is disposed over and covers the vessels or chambers (or cavities or bowls). Thus, the vessels or chambers are formed by and completely enclosed by the plastic sheet (with cavities or bowls) and the permeable membrane. The fragrance or scent of the fragrant materials can permeate through the permeable membrane over time. The permeable membrane can be planar or flat, and can define a facing direction of the cartridge or dual chamber vessel as the surface or operable surface through which the scent permeates. The vessels or chambers, or plastic thereof, can be transparent or translucent, and the fragrant material can have a color so that the fragrant material is visible through the transparent or translucent vessels or chambers. The cartridge and/or dual chamber vessel can be round or circular with a disc or puck shape. The pair of chambers or vessels can be half circular or half round with a space or gap there between with opposing walls of the vessels facing the gap and forming the divider. The cartridge and/or dual chamber vessel can be disposed in a housing.

The cartridge 14 and/or dual chamber vessel 16 can be pivotally coupled to a back plate 26. The cartridge or dual chamber vessel can face the back plate; and an inner surface of the back plate and the permeable membrane can face one another or can be disposed opposing one another, and oriented parallel with respect to one another. The back plate can form a portion of the housing. The back plate can be circular or round, and can match the shape of the cartridge or dual chamber vessel. The back plate 26 has a back opening 30 therein exposing a back of the cartridge 14 or the dual chamber vessel 16, or the permeable membrane 22 thereof. Thus, the permeable membrane can face the back opening in the back plate. The back opening 30 can have a substantial half circular or half round shape, substantially matching the shape of the chambers. In addition, the back opening 30 can be sized substantially half the size of the back plate to maximize scent release. Furthermore, the back opening 30 can be disposed in or located in a lower portion thereof to accommodate the location of the fragrant material in the vessels (which can be in the lower portions thereof due to gravity).

Figure 1:
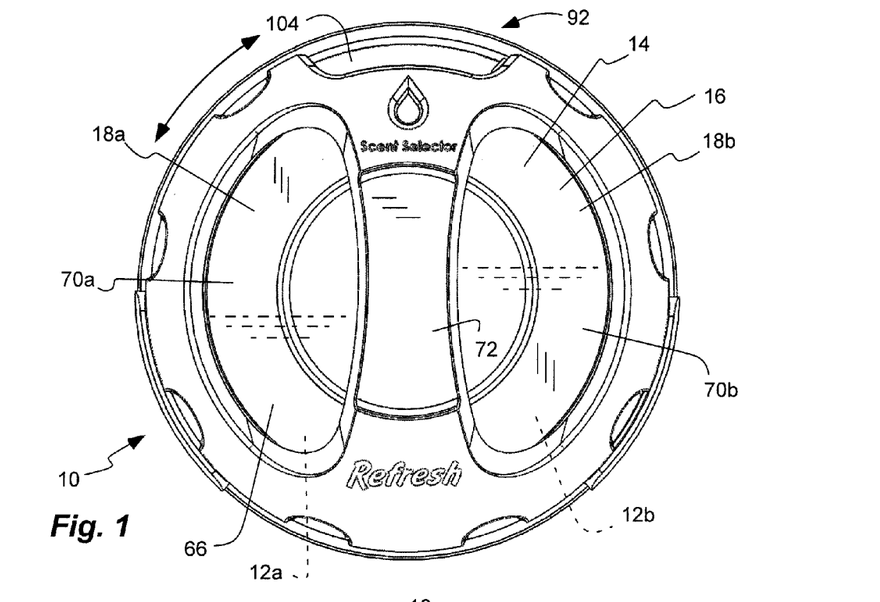
FIG. 1 is a front view of a dual scent air freshener in accordance with an embodiment of the present invention.
Figure 2:
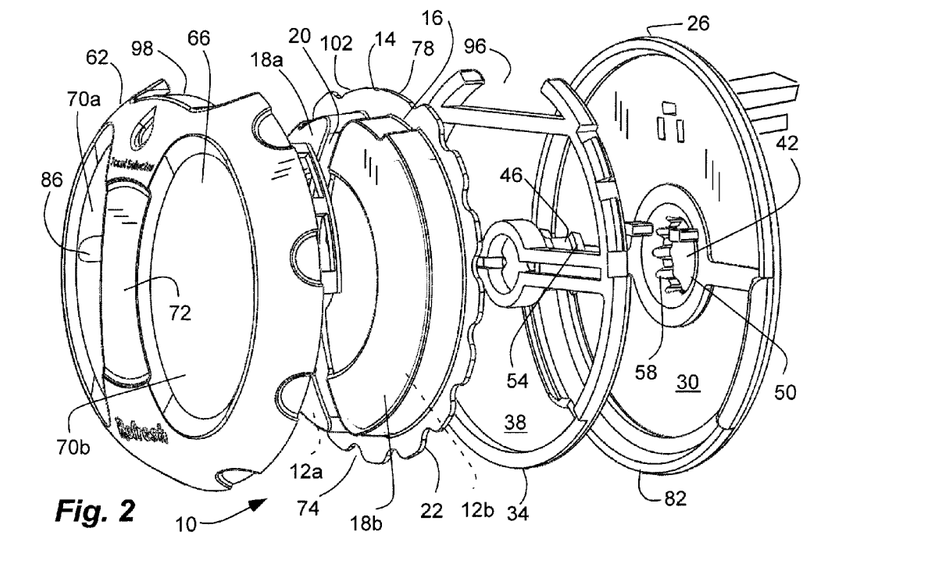
FIG. 2 is an exploded perspective view of the air freshener of FIG. 1.
Figure 3A:
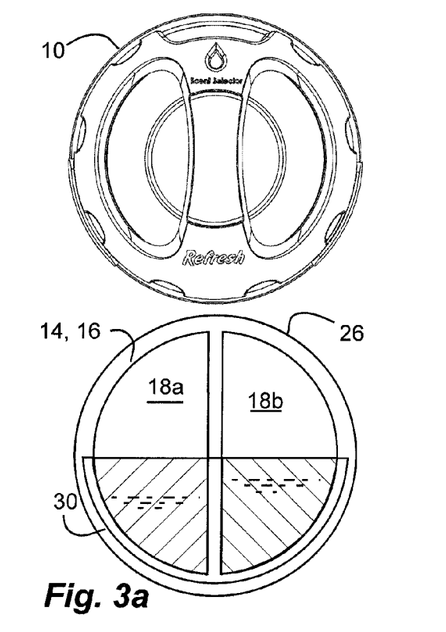
Figure 3B:
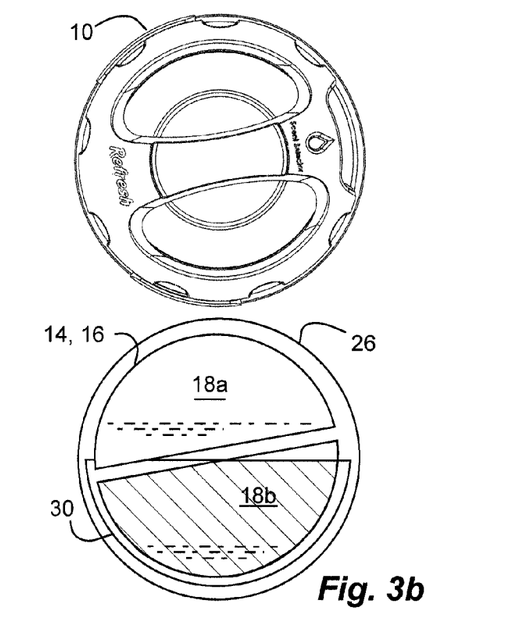
Figure 4:
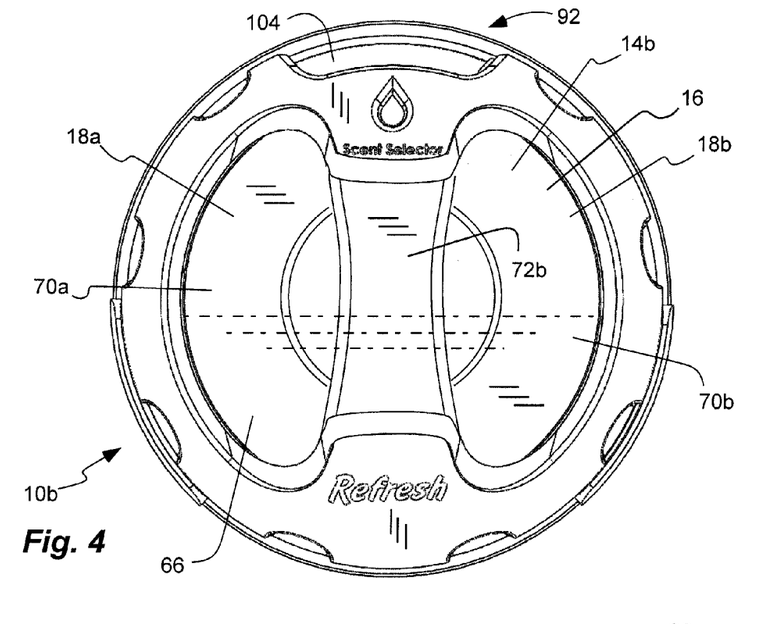
FIG. 4 is a front view of a single scent air freshener in accordance with another embodiment of the present invention.
Figure 5:
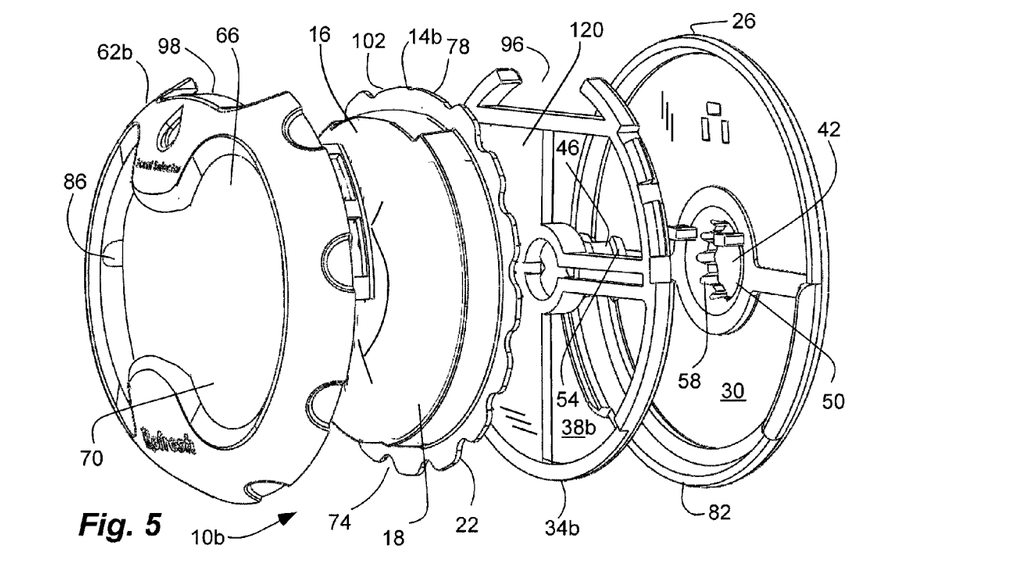
FIG. 5 is an exploded perspective view of the air freshener of FIG. 4.

The pair of chambers 18a and 18b can be separately aligned with back opening 30 to facilitate or expedite the release of the fragrance contained in the aligned chamber, as shown in FIG. 3b. In addition, both of the pair of chambers 18a and 18b can be exposed, or partially exposed, so that both fragrances can be released simultaneously, as shown in FIG. 3a. It will be appreciated that scents or fragrances can be combined in a complimentary way, e.g. berry and vanilla. Thus, the cartridge and/or dual chamber vessel can be pivotal with respect to the back opening of the back plate to selectively position the pair of scent chambers with the back opening. The cartridge and/or dual chamber vessel can have a plurality of positions, including: only one of the pair of chambers aligned with the back opening; only the other one of the pair of chambers aligned with the back opening; and a portion of both, either equally or unequally, of the chambers aligned (or partially aligned) with the back opening.

An intermediate brace 34 can be pivotally coupled to the back plate 26 and disposed between the back plate 26 and the cartridge 14 or dual chamber vessel 16. The intermediate brace can form part of the housing. The brace 34 can be pivotal with respect to the back plate, and pivotal with the cartridge or dual chamber vessel. The brace 34 can have an intermediate opening 38 therethrough to limit interference of the brace with the permeable membrane of the dual chamber vessel and its alignment with and/or exposure to the back opening. In one aspect, a majority or almost all of the intermediate brace can be open, with a center hub, a perimeter ring, and a cross brace interconnecting the hub and perimeter ring. The intermediate brace can have a round or circular shape to match the back plate and the cartridge.

A pivot 42 can be disposed between the back plate 26 and the intermediate brace 34 to pivotally couple the two together. The pivot can include a pair of prongs 46 formed on the brace 34 (or hub thereof) and pivotally disposed in a bore 50 formed in the back plate 26. It will be appreciated that the alternate configuration is also possible, i.e. the prongs extending from the back plate into a bore in the brace. In addition, one or more protrusions 54 can be formed on the prongs and receivable in one or more indentations 58 in the bore 50 or wall of the bore.

The pair of prongs can deflect inwardly as the pair of prongs pivot within the bore, and the one or more protrusions moves in and out of the one or more indentations. It will be appreciated that the alternate configuration is also possible, i.e. the protrusions formed in the bore and the indentations formed on the prongs. The protrusions 54 and indentations 58 can provide a plurality of discrete rotational positions of the brace (and thus the cartridge or dual chamber vessel) with respect to the back plate or back opening.

A front dial plate 62 can be coupled to the brace 34 and can pivot with the brace and the cartridge or dual chamber vessel with respect to the back plate 26. The front dial plate can snap fit to the brace, e.g. with teeth in the brace fitting into notches on the dial plate. The front dial plate can form part of the housing. A cavity 66 is formed between the brace 34 and the front dial plate 62, and receives the cartridge 14 or the dual chamber vessel 16. The cavity 66, and thus the cartridge 14 or dual chamber vessel 16 or membrane thereof, is exposed from behind by the back opening 30 and the intermediate opening 38. Thus, the cartridge 14 or the dual chamber vessel 16 pivots with the intermediate brace 34 and front dial plate 62 to selectively position all or a portion of one or both of the pair of chambers 18a and 18b with the back opening 30 and the intermediate opening 38. The front dial plate and/or intermediate brace can be configured to be engaged by a user's fingers to pivot or turn the front dial plate, and thus the pair of chambers, with respect to the back opening.

A pair of windows or apertures 70a and 70b can be formed in the front dial plate 62 and each aligned with a different one of the pair of chambers 18a and 18b. As indicated above, the fragrance material can be visible through the pair of chambers and through the pair of windows. The dial plate 62 can have a rib 72 or cross member bisecting the front dial plate, or opening therein, and that is flanked on both sides by the windows or openings. The rib can cover the gap or divider between the pair of chambers, and can form a knob or griping surface to facilitate turning the front dial plate.

The cartridge 14 and/or dual chamber vessel 16 can have a perimeter, flange or perimeter ring 78 that is sized to extend to an inner dimension of the cavity 66 to more firmly hold the cartridge or dual chamber vessel. In addition, the air freshener 10 can be configured to facilitate air flow through the device. One or more notches 74 can be formed in the perimeter ring 78. A gap 82 can be formed between the back plate 26 and the front dial plate 62, such as at a bottom perimeter between the two. An air flow path can be defined through the back aperture 30, through the intermediate aperture 38, through the one or more notches 74, and through the gap 82. The notches 74 can be arrayed around a perimeter to accommodate any rotational orientation of the cartridge. Furthermore, one or more tabs 86 on the front dial plate 62 can engage one or more of the notches 74 of the dual chamber vessel 14 to maintain alignment of the chambers 18a and 18b with the windows 70a and 70b, and to secure the dual chamber vessel 14 in the cavity 66 so that the dual chamber vessel pivots with the front dial plate and the brace.

In addition, the air freshener 10 can include an indicator 92 of the selected scent(s). A perimeter notch 96 and 98 can be formed in the intermediate brace 34 and the front dial plate 62. A perimeter notch 102 can also be formed in the perimeter ring 78 of the cartridge or dual chamber vessel 74. The notches can align so that a scale 104 on the back plate is visible. The scale can be disposed on the inner surface of the back plate, and along an upper perimeter thereof. Thus, the scale can have a length or arc length longer greater than the notch. The notches pivot with the front dial plate and brace so that the scale can indicate the selected scent. The scale can include indicia and can indicate the relative rotational position of the chamber(s) with the back opening. For example, the scale can include indicia indicating the selected scent, or a graphic indicating the relative percentages of the selected scents.

The air freshener 10 can be configured for use with an air vent, such as with a vehicle. Thus, a clip can connect to the back plate and can be configured to engage an air vent. The back plate can be stationary and fixed with respect to the vent, while the front dial plate, cartridge or dual chamber vessel, and intermediate brace pivot with respect to the back plate.

In use, a method for selectively providing a desired scent, includes:
   pivoting the pair of chambers with respect to the back plate so that one of the pair of chambers is substantially aligned with the back opening in the back plate to substantially disperse a first fragrance;
   pivoting the pair of chamber with respect to the back plate so that another of the pair of chambers is substantially aligned with the back opening in the back plate to substantially disperse a second fragrance; and
   pivoting the pair of chambers with respect to the back plate so that both of the pair of chambers are exposed to the back opening in the back plate to disperse both the first and second fragrances.

The back plate, intermediate brace, and front dial plate can be manufactured of injection molded plastic.

Figure 6A:
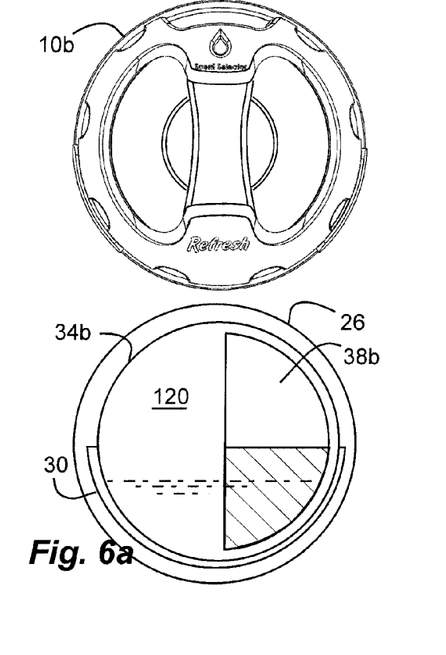
Figure 6B:
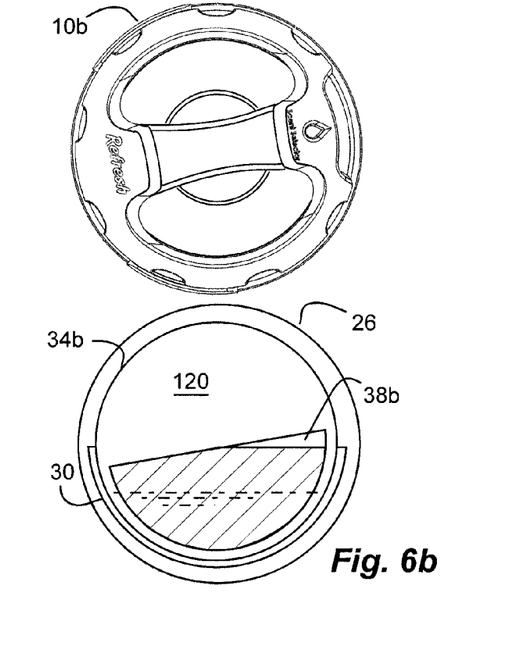

In accordance with another aspect of the present invention, and as shown in FIGS. 4-6b, an air freshener 10b can have a single scent. The air freshener can be similar to that described above, and which description is incorporated herein. The air freshener can have a cartridge 14a with a single chamber vessel 16 having a single chamber or vessel 18. The intermediate brace 34b can be or can have an intermediate or blocking plate 120 and the intermediate opening 38b can be limited to an opening only in a half or portion thereof, such as a semicircular opening corresponding or matching the back opening in the back plate. A blocking plate 120 can be formed on an opposite side of the intermediate opening 38b. Thus, the intermediate opening can be sized less than half of the intermediate brace, and the back opening can be sized less than half of the back plate. The dial plate 62b and the intermediate plate brace or plate can pivot to selectively align the intermediate opening with the back opening, as shown in FIG. 6a. The blocking plate can be pivotal between a lower position blocking the back opening (opposite that shown in FIG. 6b), and an upper position away from the back opening and with the intermediate opening aligned with the back opening, as shown in FIG. 6b. The front dial plate 62b can have a single opening or aperture or window 70. A knob 72b can be formed in the cartridge. The scale can include indicia indicating the amount of scent release selected.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a back plate having a back opening therethrough;
   b) an intermediate brace pivotally coupled to the back plate and having an intermediate opening therethrough;
   c) a front dial plate coupled to the brace and pivotal with the brace with respect to the back plate;

d) a cavity formed between the brace and the front dial plate, the cavity exposed from behind by the back opening and the intermediate opening;
e) at least one chamber disposed in the cavity and containing a fragrant material and having a permeable membrane through which a fragrance of the fragrant material can permeate over time;
f) the at least one chamber, the intermediate brace and the front dial plate being pivotal together with respect to the back plate to selectively align the at least one chamber, the intermediate opening of the intermediate brace, or both, with the back opening in the back plate;
g) a perimeter notch formed in the intermediate brace and the front dial plate extending from a perimeter of the front dial plate and the intermediate brace, and extending toward a center of the dial plate, and being rotatable therewith respect to the back plate; and
h) a scale on the back plate visible through the perimeter notch to indicate a relative rotational position of the at least one chamber, the intermediate opening of the intermediate brace, or both, with the back opening in the back plate.

2. A device in accordance with claim 1, wherein the permeable membrane is flat and faces the back opening in the back plate.

3. A device in accordance with claim 1, wherein the scale has a length greater than the perimeter notch.

4. A device in accordance with claim 1, wherein a perimeter of the at least one chamber is sized to extend to an inner dimension of the cavity, and has a plurality of notches formed therein.

5. A device in accordance with claim 1, wherein the at least one chamber further includes a vessel formed in a transparent or translucent layer and covered by the permeable membrane; and wherein the fragrant material is a colored liquid visible through the transparent or translucent layer of the vessel and a front opening in the front dial plate.

6. A device in accordance with claim 1, wherein the device is configured for a single scent and wherein:
the at least one chamber is a single chamber;
the intermediate opening in the intermediate brace and the back opening in the back plate are sized less than half of the intermediate brace and back plate, respectively; and
the dial plate and the intermediate brace pivot to selectively align the intermediate opening with respect to the back opening.

7. A device in accordance with claim 6, wherein:
the back plate is coupled to a clip configured to engage an air vent and is stationary with respect to the clip and air vent;
the back opening in the back plate is located in a lower portion thereof;
the permeable membrane is flat and faces the back plate;
the fragrant material is a liquid;
the intermediate brace has a blocking plate on a half thereof opposite the intermediate opening; and
the blocking plate of the intermediate brace is pivotal between a lower position blocking the back opening, and an upper position away from the back opening and with the intermediate opening aligned with the back opening.

8. A device in accordance with claim 1, wherein the device is configured for dual scents and wherein:
the at least one chamber includes a pair of scent chambers coupled together and disposed adjacent one another in a side-by-side relationship and formed as a pair of separate and discrete vessels in a plastic sheet separated by a divider and covered by the permeable membrane; and
the pair of scent chambers are pivotal with respect to the back plate to selectively position the pair of scent chambers with respect to the back opening between a plurality of positions including: only one of the pair of chambers aligned with the back opening, only the other of the pair of chambers aligned with the back opening, and a portion of both of the pair of chambers aligned with the back opening.

9. A device in accordance with claim 1, further comprising:
a pivot disposed between the back plate and the intermediate brace including a pair of prongs pivotally disposed in a bore, and further including one or more protrusions receivable in one or more indentations, the pair of prongs deflectable inwardly as the pair of prongs pivot within the bore and the one or more protrusions moves in and out of the one or more indentations.

10. A dual scent air freshener device, comprising:
a) a single cartridge with a pair of scent chambers coupled together and disposed adjacent one another in a side-by-side relationship and formed as a pair of separate and discrete vessels in a plastic sheet separated by a divider and covered by a permeable membrane and each of the pair of vessels containing a fragrant material with a fragrance that can permeate through the permeable membrane over time;
b) a back plate pivotally coupled with respect to the pair of chambers and having a back opening therethrough with the permeable membrane facing the back opening;
c) the cartridge being pivotal with respect to the back plate to selectively position the pair of scent chambers with respect to the back opening between a plurality of positions including: only one of the pair of chambers aligned with the back opening, only the other of the pair of chambers aligned with the back opening, and a portion of both of the pair of chambers aligned with the back opening; and
d) an intermediate brace pivotally coupled to the back plate and having an intermediate opening therethrough;
e) a front dial plate coupled to the brace and pivotal with the brace with respect to the back plate;
f) a cavity formed between the brace and the front dial plate, the cavity exposed from behind by the back opening and the intermediate opening;
g) the single cartridge is disposed in the cavity;
h) a scale indicative of the relative degree of scent material being released by each scent chamber located on an inner surface of the back plate; and
i) a perimeter notch formed on the perimeter of the front dial plate and the intermediate brace, the notch extending from a perimeter of the dial plate toward a central axis of the dial plate facilitating selection of a relative rotational position of the cartridge.

11. A device in accordance with claim 10, wherein the permeable membrane is flat and faces the back opening in the back plate.

12. A device in accordance with claim 10, wherein a perimeter of the cartridge is sized to extend to an inner dimension of the cavity, and has a plurality of notches formed therein.

13. A device in accordance with claim 10, wherein the plastic sheet is transparent or translucent; and wherein the fragrant material is a colored liquid visible through the transparent or translucent plastic sheet and a front opening in the front dial plate.

14. A device in accordance with claim 10, wherein the dial plate has a rib bisecting the dial plate and flanked on both sides by openings in the dial plate so that the cartridge is visible therethrough.

15. A device in accordance with claim 10, further comprising:
- a pivot disposed between the back plate and the intermediate brace including a pair of prongs pivotally disposed in a bore, and further including one or more protrusions receivable in one or more indentations, the pair of prongs deflectable inwardly as the pair of prongs pivot within the bore and the one or more protrusions moves in and out of the one or more indentations.

16. A dual scent air freshener device, comprising:
a) a clip configured to engage an air vent;
b) a back plate coupled to the clip and having a back opening therethrough;
c) an intermediate brace pivotally coupled to the back plate and having an intermediate opening therethrough;
d) a front dial plate coupled to the brace and pivotal with the brace with respect to the back plate;
e) a cavity formed between the brace and the front dial plate, the cavity exposed from behind by the back opening and the intermediate opening;
f) a single cartridge disposed in the cavity and having a pair of scent chambers coupled together and disposed adjacent one another in a side-by-side relationship and formed as a pair of separate and discrete vessels in a plastic sheet separated by a divider and covered by a permeable membrane and each of the pair of vessels containing a fragrant material with a fragrance that can permeate through the permeable membrane over time;
g) the permeable membrane being flat and facing the back plate;
h) the cartridge being pivotal with respect to the back plate to selectively position the pair of scent chambers with respect to the back opening between a plurality of positions including: only one of the pair of chambers aligned with the back opening, only the other of the pair of chambers aligned with the back opening, and a portion of both of the pair of chambers aligned with the back opening;
i) a perimeter notch formed in the intermediate brace and the front dial plate extending from a perimeter of the dial plate toward a central axis of the dial plate and rotatable therewith respect to the back plate; and
j) a scale on an inner surface of the back plate visible through the perimeter notch to indicate a relative rotational position of the pair of chambers with the back opening in the back plate.

17. A device in accordance with claim 16, wherein a perimeter of the cartridge is sized to extend to an inner dimension of the cavity, and has a plurality of notches formed therein.

18. A device in accordance with claim 16, further comprising:
- a pivot disposed between the back plate and the intermediate brace including a pair of prongs pivotally disposed in a bore, and further including one or more protrusions receivable in one or more indentations, the pair of prongs deflectable inwardly as the pair of prongs pivot within the bore and the one or more protrusions moves in and out of the one or more indentations.

19. A device in accordance with claim 16, further comprising:
- a pair of windows or apertures formed in the front dial plate, each aligned with a different one of the pair of chambers.

* * * * *